(12) United States Patent
Zhong et al.

(10) Patent No.: US 6,676,987 B2
(45) Date of Patent: Jan. 13, 2004

(54) COATING A MEDICAL APPLIANCE WITH A BUBBLE JET PRINTING HEAD

(75) Inventors: Sheng-ping Zhong, Northborough, MA (US); Dennis R. Boulais, Danielson, CT (US); Kshitij Mohan, Sudbury, MA (US); Michael Austin, Galway (IE); Jan Weber, Galway (IE)

(73) Assignee: SciMed Life Systems, Inc., Maple Grove, MN (US)

( * ) Notice: Subject to any disclaimer, the term of this patent is extended or adjusted under 35 U.S.C. 154(b) by 211 days.

(21) Appl. No.: 09/895,415

(22) Filed: Jul. 2, 2001

(65) Prior Publication Data

US 2003/0003220 A1 Jan. 2, 2003

(51) Int. Cl.[7] ............................................... A61L 27/00
(52) U.S. Cl. ................. 427/2.24; 427/2.1; 427/2.25; 427/2.26; 427/2.28; 427/2.3; 427/2.31; 427/258; 427/261; 427/265; 427/271; 427/272; 427/282; 427/286; 427/287; 427/307; 427/309; 427/402; 427/407.1; 427/409; 427/421; 427/422; 427/424
(58) Field of Search ....................... 427/2.1, 2.24, 427/2.25, 2.26, 2.28, 2.3, 2.31, 258, 261, 265, 271, 272, 282, 286, 287, 307, 309, 402, 407.1, 409, 421, 422, 424

(56) References Cited

U.S. PATENT DOCUMENTS

| | | | |
|---|---|---|---|
| 5,059,266 A | | 10/1991 | Yamane et al. |
| 5,804,083 A | | 9/1998 | Ishii et al. |
| 5,935,331 A | | 8/1999 | Naka et al. |
| 6,058,843 A | * | 5/2000 | Young ........................ 101/483 |
| 6,107,004 A | * | 8/2000 | Donadio, III ................ 430/320 |
| 6,176,874 B1 | | 1/2001 | Vacanti et al. |
| 6,193,923 B1 | | 2/2001 | Leyden et al. |
| 6,287,628 B1 | * | 9/2001 | Hossainy et al. ............. 427/2.3 |
| 6,395,326 B1 | * | 5/2002 | Castro et al. ............... 427/2.24 |

FOREIGN PATENT DOCUMENTS

WO      WO 01/91918      12/2001

OTHER PUBLICATIONS

Rogers, John A., "Microcontac Printing and Electroplating on Curved Substrates: Production of Free–Standing Three–Dimensional Metallic Microstructures", Adv. Mater. 1997, 9, No. 6, pp. 475–477.*

MICRODROP Brochure, "undated" "Microdosing of Liquids In The Piko–To Nanoliter–Range".

(List continued on next page.)

*Primary Examiner*—Shrive P. Beck
*Assistant Examiner*—Jennifer Kolb Michener
(74) *Attorney, Agent, or Firm*—Kenyon & Kenyon (57) ABSTRACT

System and method for coating a medical appliance is provided. In accord with one embodiment, a system for applying a coating to a medical appliance having accessible patterned surfaces is provided. This system may include: a processor, a support, and a bubble jet printing head having individual printing nozzles. In this system the support may be adapted to hold the medical appliance and to provide direct access for a coating to contact the exposed external patterned surfaces of the medical appliance. The bubble jet printing head in this system may move with respect to the medical appliance and may be in communication with a source of coating and with the processor. The processor in this system may contain commands that instruct the bubble jet printing head to force coating onto the accessible patterned surfaces of the medical appliance in a pattern that correlates with the accessible patterned surfaces of the medical appliance.

16 Claims, 7 Drawing Sheets

OTHER PUBLICATIONS

P. F. Blazdell, et al., "Application of a continuous ink jet printer to solid freeforming of ceramics", Journal of Materials Processing Technology 99, (2000) pp. 94–102.

Jin Hua Song et al., "Formulation and Multilayer Jet Printing of Ceramic Inks", Journal of the American Ceramic Scoiety Incorporating Advanced Ceramic Materials and Communications, vol. 82, No. 12, Dec. 1999, pp. 3374–3380.

Matthew Mott, et al., "Microengineering of Ceramics by Direct Ink–Jet Printing", Journal of the American Ceramic Scoiety Incorporating Advanced Ceramic Materials and Communications, vol. 82, No. 7, Jul. 1999, pp. 1653–1658.

M. J. Wright, et al., "Ceramic Deposition using and Electromagnetic Jet Printer Station,", Journal of Materials Science Letters 18, (1999), pp. 99–101.

D. A. Grigoriev, et al., "Preparation of Silicon Carbide by Electrospraying of a Polymeric Precursor", vol. 81, No. 4, (2001), pp. 285–291.

P. Miao, "Electrostatic Atomization of Ultra Fine Spray of Ceramic Solution", Institute of Physics Conference Series No. 163, Proceedings of the 10$^{th}$ International Conference, Combridge Mar. 28–31, 1999, pp. 119–122.

Kitty A. M. Seerden, et al., "Ink Jet Printing of Wax–Based Alumina Suspensions", Journal of the American Ceramic Scoiety Incorporating Advanced Ceramic Materials and Communications, vol. 84, No. 11, Nov. 2001, pp. 2514–2520.

J. R. G. Evans, et al., "Combinatorial Searches of Inorganic Materials using the Ink–Jet Printer: Science, Philosophy and Technology", Journal of the European Ceramic Society, vol. 21, No. 13, (2001), pp. 2291–2299.

P. F. Blazdell, et al., "Preparation of Ceramic Inks for Solid Freeforming Using a Continuous Jet Printer", Journal of Materials Synthesis and Processing. vol. 7, No. 6, Nov. 1999, pp. 349–356.

J. A. Rogers, et al., "Microcontract Printing and Electroplating on Curved Substrates: Production of Free–Standing Three–Dimensional Metallic Microstructures", Advanced Materials, 1997, vol. 9, No. 6, pp. 451–477.

Rogers J. A. et al., "Microcontract Printing and Electroplating on Curved Substrates: Production of Free–Standing Three–Dimensional Metallic Microstructures", Advanced Materials, VCH Verlagsgesellschaft, Weinheim, DE, vol. 9, No. 6, pp. 475–477 (May 1, 1997)* Mentioned in the Search Report.

* cited by examiner

COATING A MEDICAL APPLIANCE WITH A BUBBLE JET PRINTING HEAD

FIELD OF THE INVENTION

The present invention generally regards the coating of work-pieces. More particularly, the present invention regards method and system for precision coating implantable medical appliances.

BACKGROUND

The positioning and deployment of medical appliances within a target site of a patient is a common, often-repeated procedure of contemporary medicine. These appliances or implants are used for innumerable medical purposes including the reinforcement of recently re-enlarged lumens and the replacement of ruptured vessels.

Coatings are often applied to these medical appliances to increase their effectiveness. These coatings may provide a number of benefits including reducing the trauma suffered during the insertion procedure, facilitating the acceptance of the medical appliance into the target site, and improving the post-procedure effectiveness of the appliance.

Expandable stents, stent grafts, balloon delivery systems, and aneurism coils are specific examples of medical appliances or implants that may be coated and inserted within the body. Expandable stents are tube-like medical appliances that often have a mesh-like structure designed to support the inner walls of a lumen. These stents are typically positioned within a lumen and, then, expanded to provide internal support for it. Because of the direct contact of the stent with the inner walls of the lumen, stents have been coated with various compounds and therapeutics to enhance their effectiveness.

When this coating is haphazardly applied or has somehow been removed during the stent's manufacture or delivery, the stent's effectiveness can be compromised. In certain circumstances, defective implanted stents must be removed and replaced through a second medical procedure—an unwanted result.

Indiscriminate coating methods such as dip-coating and spray-coating have been used to coat stents as well as other medical appliances. These methods are, however, both wasteful and difficult to control. For example, dipping can result in non-uniform application of the coating to the appliance, thereby placing more coating at one end or region of the stent and making it difficult to predict the dosage of therapeutic that will be delivered when the stent or other appliance is implanted. The indiscriminate nature of dipping is also problematic as it may lead to the cracking and crumbling of coating at the junctions, hinges, and flexing members of the mesh-like stents. The coating that covers the hinged portions of the stent is highly susceptible to be exfoliated because, as the stent is expanded, intolerable stresses may develop within the coating.

Figure 1:
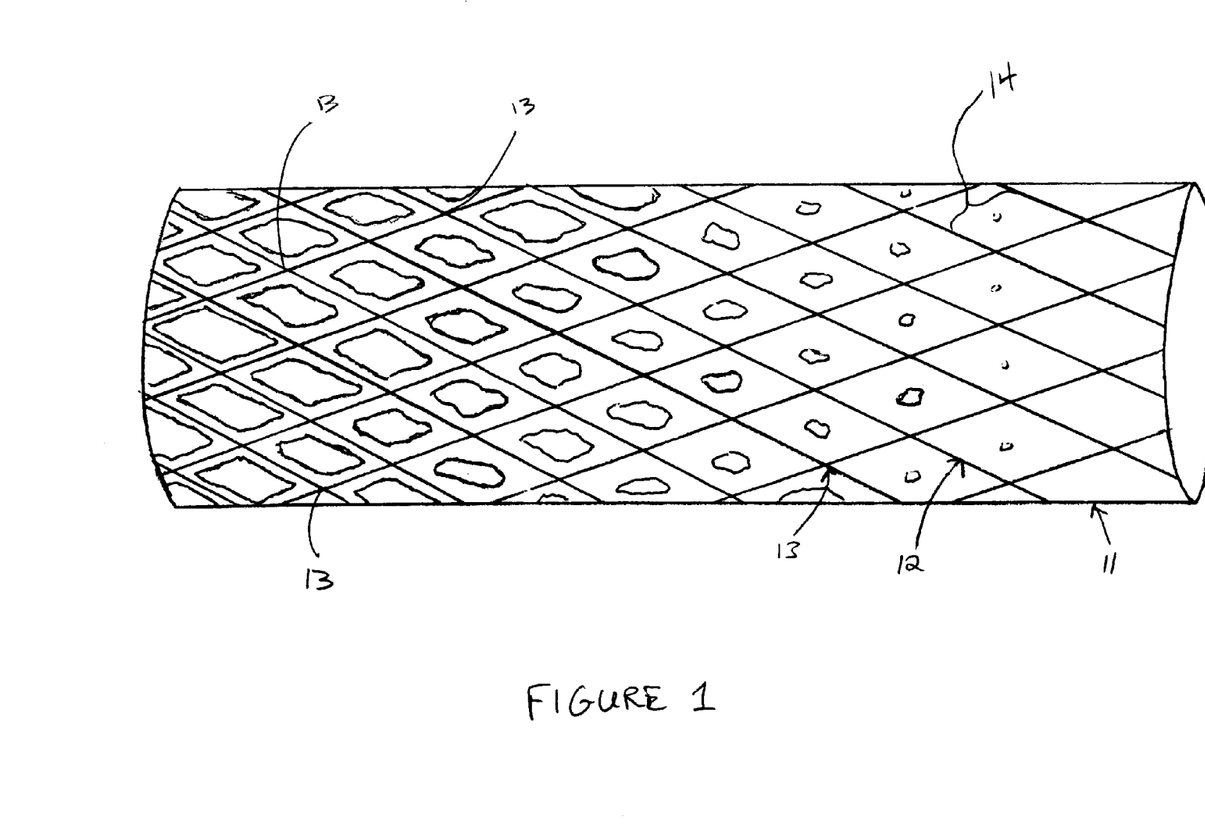
FIG. 1 is an enlarged view of a stent that has been unevenly coated with a coating.
Figure 2:
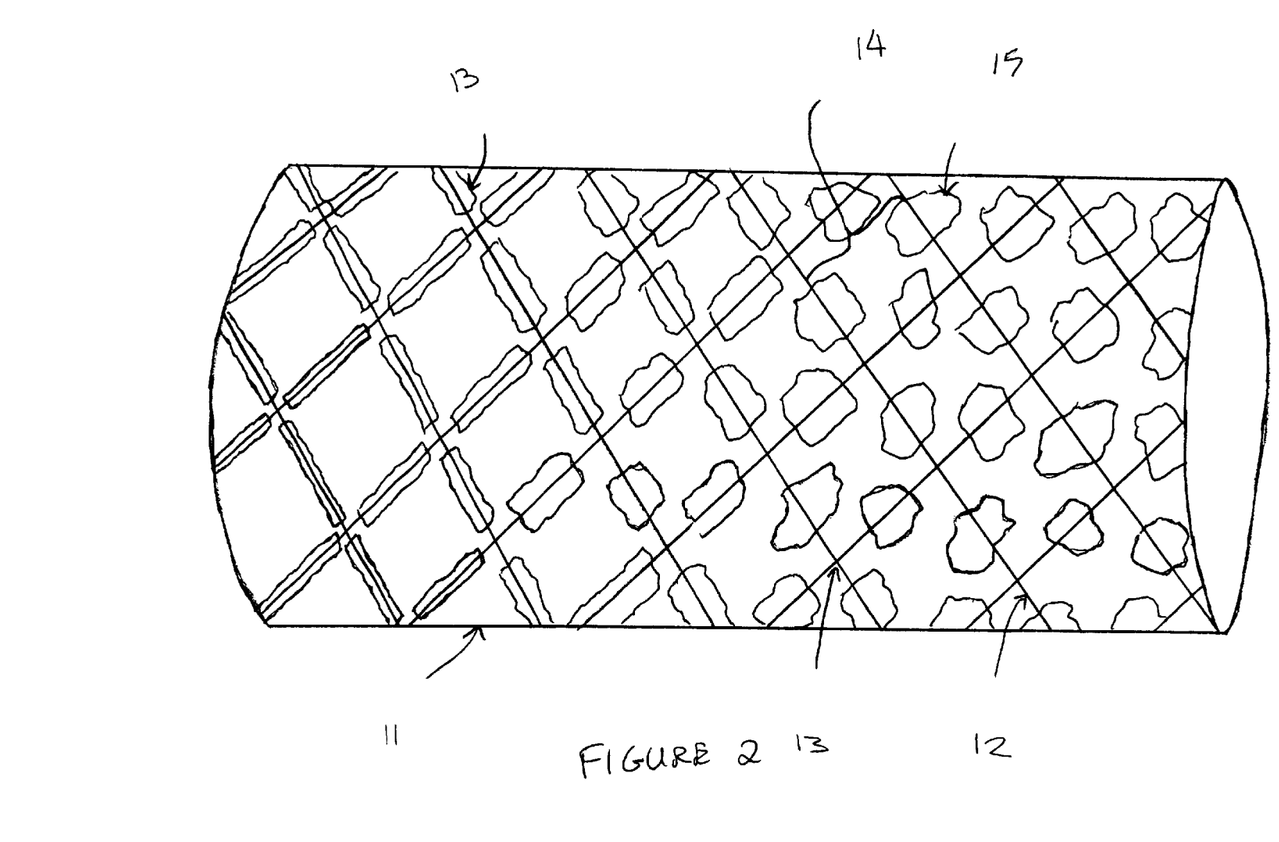
FIG. 2 is an enlarged view of the stent of FIG. 1 in an expanded state, the uneven coating being broken and cracked at the junction of the stent's struts.

FIGS. 1 and 2 are illustrative of some of the concerns stemming from an indiscriminate coating process like dipping. In FIG. 1 stent 11 is shown in a closed, pre-deployment state. Here, the stent 11 has been previously dipped in a vat of therapeutic in the direction of arrow 16. In other words, the right side of the stent was the leading edge of the stent entering the dipping vat. As can be seen, the coating of stent 11 is heavier on the right side of the stent 11 than on the left side and covers each of the junctions 13 throughout the entire stent 11. As can also be seen, the coating becomes progressively thicker and covers more of the space between each of the struts 12 as one travels from the left side of the stent 11 to the right side of the stent 11. This increasing thickness of coating is indicative of a stent 11 that has been dipped and left stand on one of its ends as the coating dries and adheres to the stent 11.

FIG. 2 shows the unevenly coated stent 11 of FIG. 1 in an expanded state as it may be after it is positioned within the body. As is evident, the expansion of stent 11 has led to the cracking and crumbling of coating 15. Also evident is that the coating has been removed from most if not all of the junction points 13 after the stent has been expanded.

SUMMARY OF THE INVENTION

System and method for coating a medical appliance is provided. In accord with one embodiment, a system for applying a coating to a medical appliance having accessible patterned surfaces is provided. This system may include: a processor, a support, and a bubble jet printing head having individual printing nozzles. In this system the support may be adapted to hold the medical appliance and to provide direct access for a coating to contact the exposed external patterned surfaces of the medical appliance. The bubble jet printing head in this system may move with respect to the medical appliance and may be in communication with a source of coating and with the processor. The processor in this system may contain commands that instruct the bubble jet printing head to force coating onto the accessible patterned surfaces of the medical appliance in a pattern that correlates with the accessible patterned surfaces of the medical appliance.

A method for applying a coating to a medical appliance having an accessible patterned surface is also provided. In one embodiment this method may include holding the medical appliance, providing direct access to the external surfaces of the medical appliance, and receiving command signals that instruct the bubble jet printing head to force coating onto the accessible patterned surfaces of the medical appliance in a pattern that correlates with the accessible patterned surfaces of the medical appliance.

DETAILED DESCRIPTION

Figure 3:
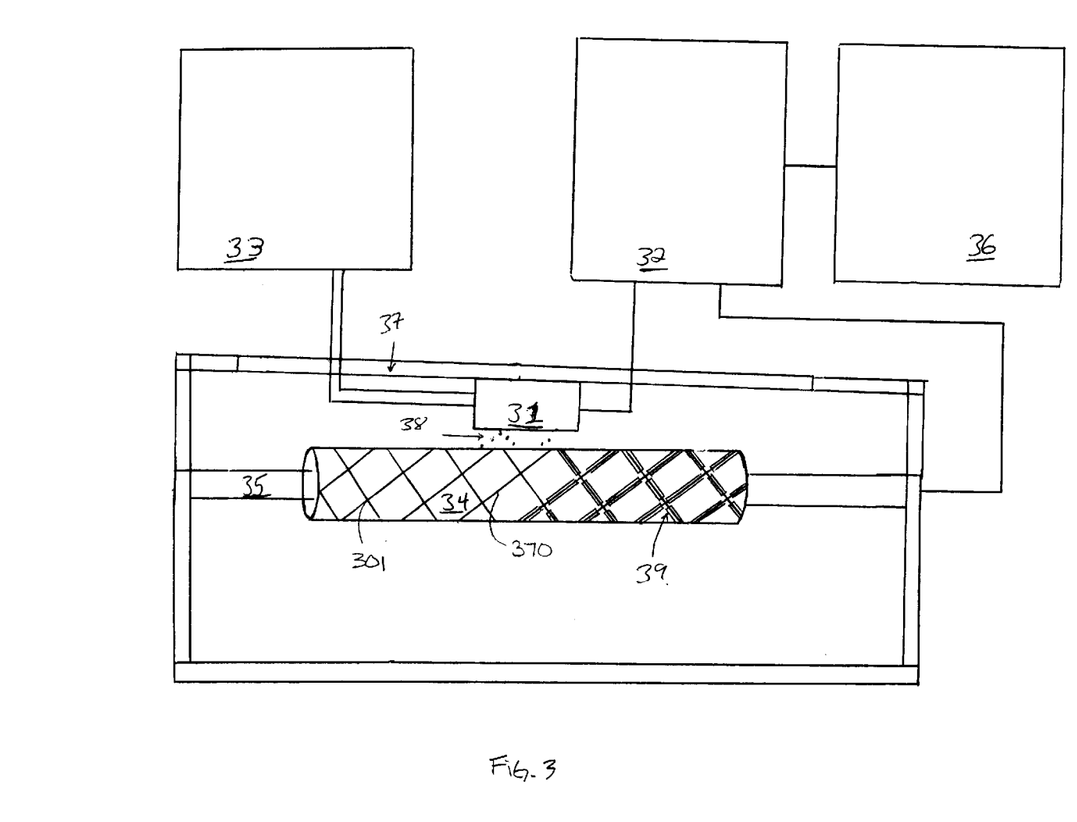
FIG. 3 is a schematic view of a system for applying a coating to a medical appliance using a bubble jet printer head in accord with one embodiment of the present invention.

FIG. 3 illustrates a system for coating a medical appliance using a bubble jet printer head in accord with one embodiment of the present invention. In this system bubble jet printer head 31 may be used to force coating onto the patterned surfaces of the medical appliance 34. In this embodiment the head 31 may be placed in close proximity to medical appliance 34 and may be moved back and forth along track 36 so that it may be able to coat the entire external patterned surface of the medical appliance 34. The printer head 31 may be controlled by or at least receive signals from processor 32, which instructs it to coat only the struts 370 of the medical appliance 34. In other words, as the bubble jet printer head 31 slides back and forth along track 37 and as the medical appliance 34 is spun on support 35, the head 31 may force coating onto the struts while concurrently refraining from forcing coating into spaces between the struts 370, because coating forced into these spaces would simply be wasted or result in errant deposits of coating elsewhere on the stent.

As can be seen in FIG. 3, a portion 39 of the struts 37 have already been coated, while other portions of the struts 37 have not. Also apparent in this Figure is that the junctions 301 of struts 370 have not been coated.

In FIG. 3 the coating source 33 may be in fluid communication with the head 31 and may be used to supply coating to the head 31. The storage media 36 may be in communication with the processor 32 and may be used to store and provide instructions for the processor 32 and the coating source 33 for coating the medical appliance 34. The storage media may be one of numerous types of available storage media including both volatile (i.e. RAM) and non-volatile storage devices (i.e. ROM, CD ROM, EEPROM, Magnetic Media, etc.). The pre-programmed instructions or other retained data may be unique to each medical appliance and may account for the unique external pattern and precise dimensions of each medical device that may be coated by the printer head 31. The storage media 36 may also hold unique instruction sets for many different medical appliances or may be provided with a media receptacle such as a disk drive that accommodates different recordable media, each recordable media holding a unique instruction set for a single medical appliance or for multiple medical appliances.

As mentioned above, the medical appliance 34 in this embodiment may be rotated by the support 35 in order to expose different sides of the medical appliance 34 to the bubble jet printer head 31. Consequently, through the coordinated movement of the bubble jet printer head 31 on track 37 and the medical appliance 34 in support 35, all external portions of the medical appliance 34 may be exposed to and coated by the nozzles (not shown) of the bubble jet printer head 31.

In an alternative embodiment, wherein the medical appliance is flat or otherwise linear, the support configuration may be different than that described above. Here, the support may provide for movement of the appliance in both the x and y planes while the printer head moves back an forth overhead in order to reach the entire surface of the medical device.

As described above, bubble jet printing head 31 may be in fluid communication with a coating source 33. This coating source 33 may contain any one of p several possible coatings to be placed on medical appliance 34. These coatings could include paclitaxel, a polymer with a suspended therapeutic, a non-thrombogenic agent, a lubricious material, a non-slippery material, a radiopaque agent, a radioactive agent, and a magnetic signature agent. These coatings could also include: pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinbiastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chioromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof Cells may be of human origin (autologous or allogenic) or from an animal source (xenogeneic), genetically engineered if desired. The delivery medium is formulated as needed to maintain cell function and viability. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

The bubble jet printer head in this embodiment is preferably programmed to coat in a precise manner, allowing coating to be applied in a complex pattern, a pattern that matches the complex pattern of the medical appliance. It is also preferred that the droplets forced from the printer head be small in relation to the target area of the medical appliance to allow for a high degree of precision in coating the target. Precision coating of the medical appliance is preferable for the economical use of coating materials.

In an alternative embodiment, rather than having the coating material deposited in one coat or layer around the entire device, the bubble jet printer head may coat the medical appliance with different layers of different thicknesses in different regions of the appliance as may be desirable for the subsequent use of the appliance. In doing so, different concentrations of therapeutic may be deposited in different regions of the medical appliance.

The coatings that may be applied by this printing jet may also include: lubricious coatings to reduce the stress exerted on the stent during the stent's deployment; radiopaque coatings for identifying the location of stents after implantation using traditional radiography techniques; radioactive agents that are useful in preventing tissue regrowth in and around implanted stents; and, magnetic coatings that enable identification of the location of the implanted stent using Magnetic Resonance Imaging (MRI) techniques. These magnetic coatings may be obtained using ferritic powders or paramagnetic powders such as Gadolinium or Disprosium.

Another useful application of this precise coating method may be to convey information, or an identification code on the appliance itself. This information or code may then be used to identify the source of the medical appliance and other history related to it for tracking purposes. Once implanted, the code, which may be a bar code, could be read though radiography, MRI or any other suitable invasive or non-invasive procedure.

Figure 4:
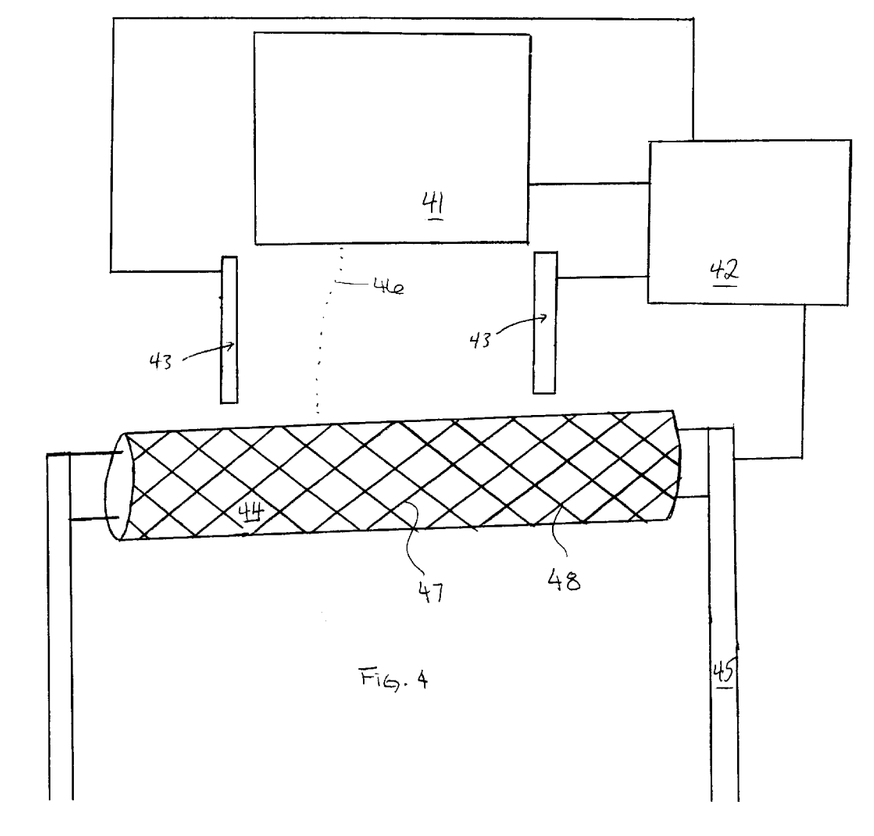
FIG. 4 is a schematic view of a system for applying a coating to a medical appliance using a bubble jet printer head in accord with another embodiment of the present invention.

FIG. 4 shows a system for coating a medical appliance using a bubble jet printer head and means for redirecting the material forced from the bubble jet printer head prior to impacting the targeted medical appliance in accord with an alternative embodiment of the present invention. In this embodiment the bubble jet printer head 41 may be used to coat a medical appliance 44 as described above. However, in this embodiment, after individual bubbles of coating 46 have been forced from the printer head 41 they may be redirected or influenced by the redirecting means 43. These redirecting means 43 can be implemented using an electromagnetic field generator or an airstream jet as well as any other suitable methods that may influence the path or trajectory of the coating once it has been forced from the head 41. By employing these means 43 the distance that the head may travel may be reduced. Similarly, the head may not need to be moved back and forth as quickly as in earlier embodiments as the gross adjustments may be completed with the movement of the head 41 along a track while the finite adjustments of the forced coating may be controlled by the means 43.

In this embodiment, bubble jet printer head 41 may be controlled by the processor 42, which may also control support 45 and means 43. Here, the bubble jet printing head, working in concert with the support 45, which may hold, move, and rotate the medical appliance 44, may coat each of the struts 47 but not the junctions 48 as shown in the Figure. The means 43 may be mounted so that material forced from bubble jet printer head 41 passes between them before reaching medical appliance 44. Alternatively, if the means were to employ air pressure or some other sort of fluid force, only one means 43 may be required.

Figure 5:
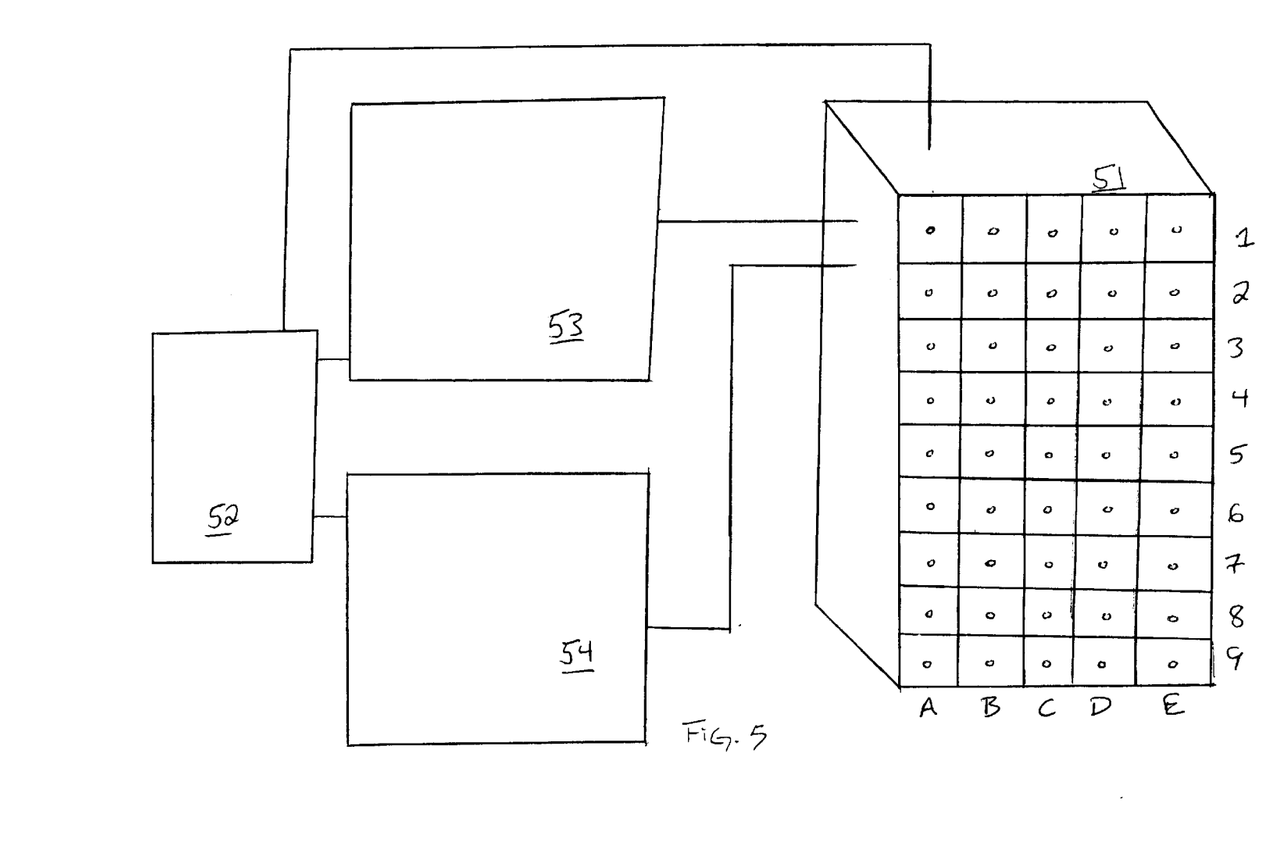
FIG. 5 is a schematic view of a bubble jet printer head in fluid communication with two coating sources in accord with another embodiment of the present invention.

FIG. 5 shows an alternative embodiment of the present invention wherein the printer head 51 is in fluid communication with two sources of coating 53 and 54. In FIG. 5 bubble jet printer head 51 is shown from below, from the perspective of the medical appliance. As can be seen, a matrix of nozzles may be arrayed on the bottom face of bubble jet printer head 51. This matrix may be labeled on the horizontal axis A–E and on the vertical axis 1–9.

Bubble jet printer head 51 may be controlled by processor 52 and may be in fluid communication with the first coating source 53 and the second coating source 54. In this exemplary embodiment, each of the nozzles in the matrix may be in fluid communication with first coating source 53 and the second coating source 54 and may be able to selectively force material from first coating source 53 and second coating source 54 onto a medical appliance that is being coated. Thus, as necessary, nozzle B-3 may force coating from first coating source 53 and then from second coating source 54 on to the appliance. Alternatively, a first group or set of the nozzles in the matrix may work in conjunction with one another and the first coating source 53 while a second group of nozzles may work together and be in fluid communication with another and the second coating source 54. Then, as required, the individual groups can work in concert with one another to coat the work-piece or medical appliance. Here, the first group of nozzles may be defined as any combination of the nozzles in the matrix, including but not limited to whole rows, whole columns, and alternating rows and columns to produce a checkerboard pattern. This embodiment, thus, makes possible the application of multiple coatings of multiple materials to a medical appliance in a precise manner in one process step.

Figure 6:
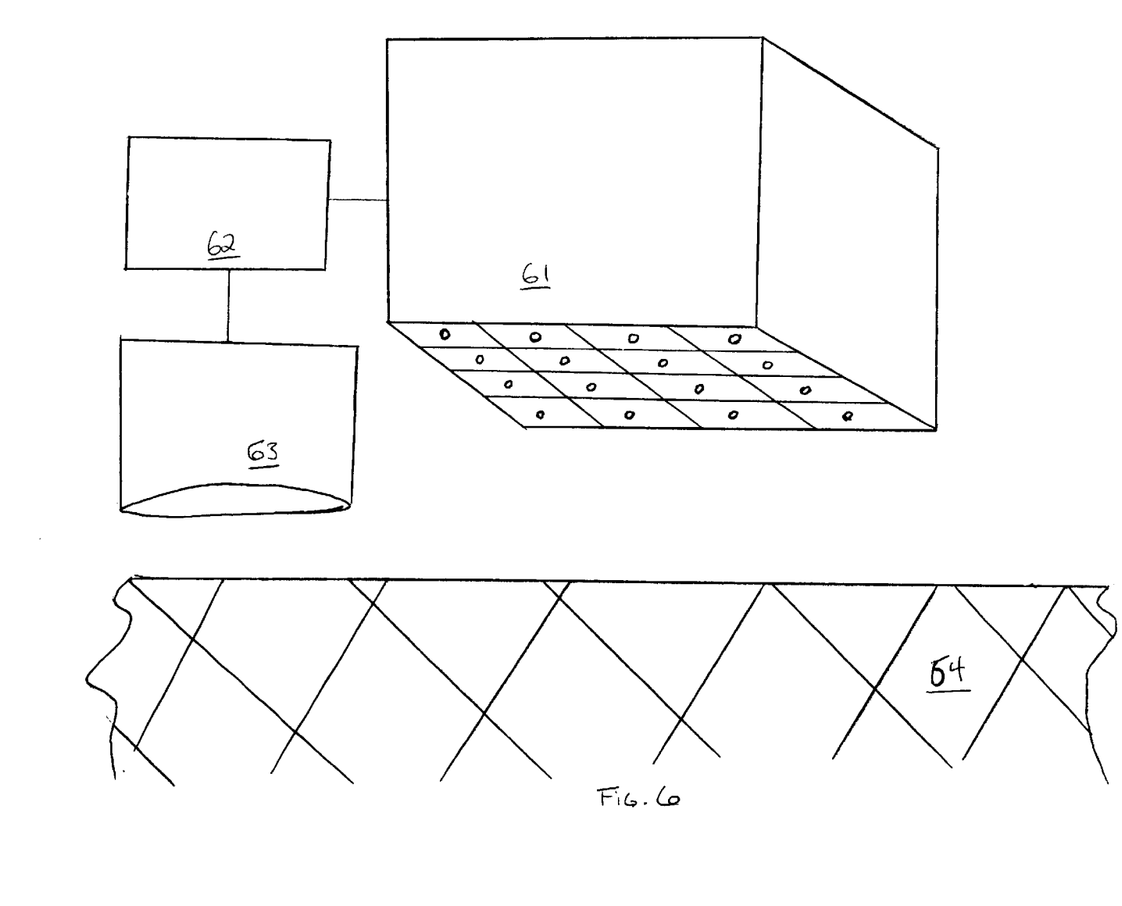
FIG. 6 is a schematic view of a system for applying a coating to a medical appliance using a bubble jet printer head and incorporating a microvision system in accord with another embodiment of the present invention.

FIG. 6 illustrates an alternative embodiment of the present invention. In FIG. 6, bubble jet printer head 61 is shown from a side perspective view with the bottom face visible and showing the matrix of nozzles. Opposite the matrix of nozzles on bubble jet printer head 61 is medical appliance 64 held in a support (which is not shown). Also evident in FIG. 6 is microvision system 63. This system 63 may be any number of optical observation systems including those employing laser scanners and video cameras as well as both visible and invisible light scanners. This system 63 may be used to observe the deposition of the coating onto the medical appliance 64 as well as to perform numerous other functions including verifying the position of the head 61 and the appliance 64. In this embodiment, the microvision system 63 may be used for quality control, for orienting the medical appliance 64 with respect to the bubble jet printer head 61, and for tracking the external pattern of medical appliance 64 during the coating process. Therefore, processor 62 may use information received from microvision system 63 to adjust the commands it issues to bubble jet printer head 61 during the coating process.

Figure 7:
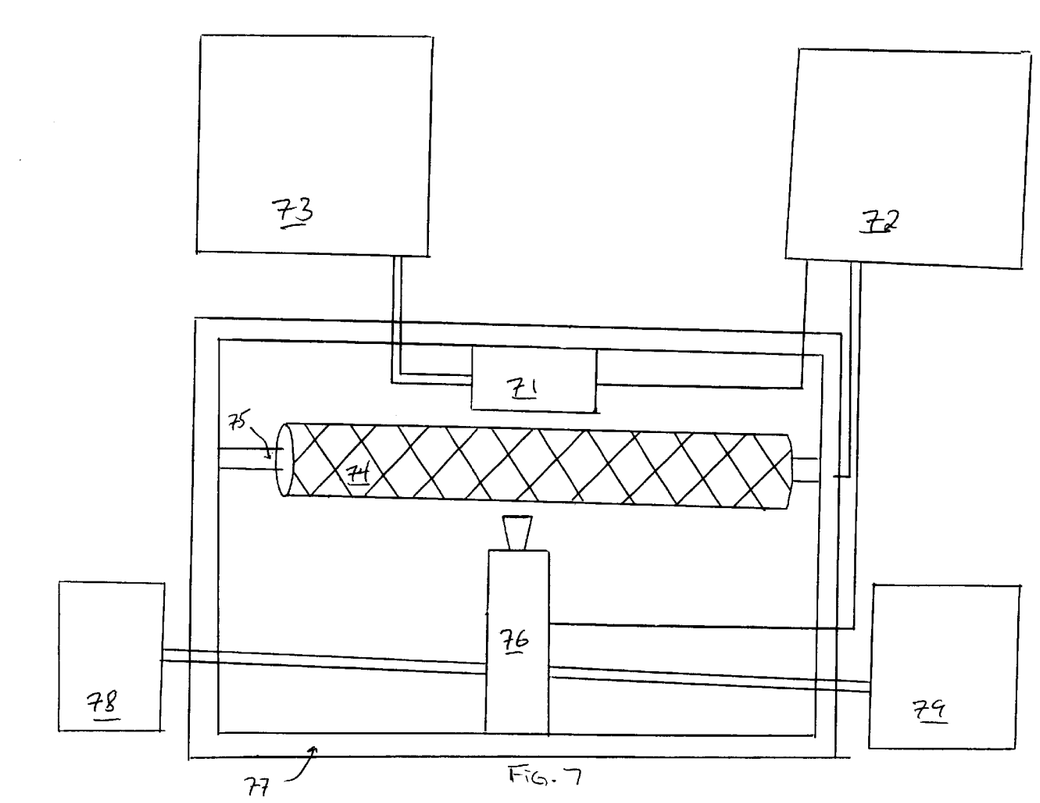
FIG. 7 is a schematic view of a system for applying a coating to a medical appliance using a bubble jet printer head in accord with another embodiment of the present invention.

FIG. 7 shows a system for coating a medical appliance using a bubble jet printer head in accord with another alternative embodiment of the present invention. Bubble jet printer head 71 is shown in FIG. 7 as being mounted on support 77 and in fluid communication with coating source 73. Also evident in FIG. 7 are appliance support 75, sprayer 76, first sprayer source 78, and second sprayer source 79.

In this embodiment, rather than applying a coating material with the head 71 a masking material may be applied. Once applied in a desirable pattern on the appliance 74, an etchant may then be applied with sprayer 76 to etch the exposed portions of the appliance 74 thereby etching the appliance in all regions not covered by the masking material. Then, once all the required etching is completed the masking material may be removed.

The sprayer 76 in this embodiment may be mounted on support 77 and may be able to slide back and forth along this support during the spraying activities. The sprayer 76 may also be in fluid communication with first and second sprayer sources, similar to the coating sources described above, which may store different etching materials for use in the process.

The sprayer in this embodiment may also be used for other indiscriminate spraying applications as well, including direct etching and cleaning the medical appliance. In a direct etching application the bubble jet printer head 71 may be used to apply a corrosive material onto the medical appliance 76. Here the corrosive material may be used to selectively etch or groove portions of the various struts of the medical appliance. Alternatively, the printer head 71 may apply a first material to specific areas to be etched and, then, may apply a second material, which reacts with the first material, to etch the desired portions of the appliance.

A bubble jet printer head for coating a medical appliance is provided herein. While several embodiments have been discussed, others, within the invention's spirit and scope, are also plausible. For example, while one printer head is described in each of the above embodiments more than one printer head may also be employed. Here in this alternative embodiment, the multiple printer heads may work synchronously and asynchronously and may be ganged together to coat several appliances simultaneously.

What is claimed is:

1. A method for applying a coating to a medical appliance comprising the steps of:
   placing the medical appliance in a supporting device;
   placing a first agent into a first chamber connected to a bubble jet printing head, the bubble jet printing head including a matrix of nozzles;
   transporting the first agent from the first chamber to the bubble jet printing head;
   moving the bubble jet printing head with respect to the medical appliance;
   forcing the first agent from the bubble jet printing head through the matrix of nozzles onto the medical appliance to form a first coating and
   forcing a second agent onto the medical appliance to form a second coating, wherein at least one of the first agent and the second agent includes a corrosive material that etches the medical appliance.

2. The method of claim 1 wherein the moving and forcing are modulated so that at least one of a portion of the first coating and a portion of the second coating has a thickness that varies as a function of their position on the medical appliance.

3. The method of claim 1 wherein at least one of the first coating and the second coating is a masking material.

4. The method of claim 1 wherein at least one of the first coating and the second coating communicates information about the medical appliance.

5. The method of claim 1 wherein the first agent includes at least one of:
   a drug suspended in a polymer, a non-thrombogenic agent, a lubricious material, a non-slippery material, a radioactive agent, and a magnetic material.

6. The method of claim 1 wherein the first agent includes a radiopaque agent.

7. The method of claim 1 wherein the first coating includes a corrosive material that etched the medical appliance.

8. The method of claim 1 wherein the moving and forcing are modulated so that the first coating has a thickness that varies as a function of position on the medical appliance.

9. The method of claim 1 wherein the first coating is a masking material.

10. The method of claim 1 wherein the first coating communicates information about the medical appliance.

11. The method of claim 1 wherein at least one of the first agent and the second agent includes at least one of:
   a drug suspended in a polymer, a non-thrombogenic agent, a lubricious material, a non-slippery material, a radioactive agent, and a magnetic material.

12. The method of claim 1 wherein at least one of the first agent and the second agent includes a radiopaque agent.

13. The method of claim 1 wherein the first agent includes a therapeutic agent.

14. The method of claim 1 wherein the second agent includes a therapeutic agent.

15. The method of claim 1 wherein the moving of the bubble jet printing head with respect to the medical appliance includes rotating by the bubble jet printing head around the medical appliance.

16. The method of claim 1 wherein the moving of the bubble jet printing head with respect to the medical appliance includes rotating the medical appliance with respect to the bubble jet printing head.

* * * * *

UNITED STATES PATENT AND TRADEMARK OFFICE
CERTIFICATE OF CORRECTION

PATENT NO. : 6,676,987 B2
DATED : January 13, 2004
INVENTOR(S) : Zhong et al.

It is certified that error appears in the above-identified patent and that said Letters Patent is hereby corrected as shown below:

Title page,
Item [75], Inventors, add -- Ron Sahatjian, Lexington, MA (CN) --
Item [56], References Cited, OTHER PUBLICATIONS, "Rogers, John A.," reference, change "Microcontac" to -- Microcontact --;

Column 3,
Line 63, change "any one of p several" to -- any one of several --;

Column 4,
Line 13, change "viral, liposomes" to -- viral liposomes --;
Line 43, change "Warafin" to -- Warfarin --.

Signed and Sealed this

Sixth Day of April, 2004

JON W. DUDAS
*Acting Director of the United States Patent and Trademark Office*